US008747448B2

(12) United States Patent
Argentine

(10) Patent No.: US 8,747,448 B2
(45) Date of Patent: Jun. 10, 2014

(54) STENT GRAFT DELIVERY SYSTEM

(75) Inventor: Jeffery Argentine, Petaluma, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 527 days.

(21) Appl. No.: 12/771,077

(22) Filed: Apr. 30, 2010

(65) Prior Publication Data

US 2011/0270371 A1 Nov. 3, 2011

(51) Int. Cl.
*A61F 2/06* (2013.01)

(52) U.S. Cl.
USPC ........................................ 623/1.11; 623/1.23

(58) Field of Classification Search
CPC ........... A61F 2/95; A61F 2/954; A61F 2/958; A61F 2/962; A61F 2/966; A61F 2002/9517
USPC ............. 604/19, 93.01, 95.01, 264, 523, 528; 606/108; 623/2.11, 1.11–1.14, 623/1.2–1.23
See application file for complete search history.

(56) References Cited

U.S. PATENT DOCUMENTS

| | | | |
|---|---|---|---|
| 1,827,497 A | 10/1931 | Varney | |
| 4,723,938 A | 2/1988 | Goodin et al. | |
| 4,832,692 A | 5/1989 | Box et al. | |
| 4,990,151 A | 2/1991 | Wallsten | |
| 5,017,259 A * | 5/1991 | Kohsai | 156/294 |
| 5,137,514 A | 8/1992 | Ryan | |
| 5,197,971 A | 3/1993 | Bonutti | |
| 5,215,523 A | 6/1993 | Williams et al. | |
| 5,259,838 A | 11/1993 | Taylor et al. | |
| 5,263,969 A | 11/1993 | Phillips | |
| 5,344,426 A | 9/1994 | Lau et al. | |
| 5,345,927 A | 9/1994 | Bonutti | |
| 5,358,496 A | 10/1994 | Ortiz et al. | |
| 5,415,664 A | 5/1995 | Pinchuk | |
| 5,433,723 A | 7/1995 | Lindenberg et al. | |
| 5,449,344 A | 9/1995 | Taylor et al. | |
| 5,462,659 A | 10/1995 | Saxena et al. | |
| 5,507,727 A | 4/1996 | Crainich | |
| 5,507,768 A | 4/1996 | Lau et al. | |
| 5,534,007 A | 7/1996 | St. Germain et al. | |
| 5,571,168 A | 11/1996 | Toro | |
| 5,683,451 A | 11/1997 | Lenker et al. | |
| 5,693,084 A | 12/1997 | Chuter | |

(Continued)

FOREIGN PATENT DOCUMENTS

| | | |
|---|---|---|
| DE | 20000659 | 5/2001 |
| EP | 1302178 A2 * | 4/2003 |
| EP | 1358903 | 12/2004 |
| WO | WO 2005067819 A1 * | 7/2005 |

*Primary Examiner* — Katherine Dowe
*Assistant Examiner* — Kendra Obu

(57) ABSTRACT

A stent graft delivery system including a tip assembly, a middle member tube, a sheath assembly, and a unitary front grip. The sheath tube is axially slideable within the distal front grip lumen, the threaded assembly distal end is disposed in the proximal front grip lumen and fixed to the unitary front grip, and the first threaded tube portion and the second threaded tube portion are radially compressed together by the unitary front grip. The sheath handle engages the exterior thread of the threaded assembly in a first configuration to move the sheath tube axially relative to the middle member tube and tip tube through rotation of the sheath handle and disengages the exterior thread of the threaded assembly in a second configuration to move the sheath tube axially relative to the middle member tube and tip tube through axial motion of the sheath handle.

13 Claims, 5 Drawing Sheets

(56) References Cited

U.S. PATENT DOCUMENTS

| | | | |
|---|---|---|---|
| 5,700,269 A * | 12/1997 | Pinchuk et al. | 606/108 |
| 5,707,376 A | 1/1998 | Kavteladze et al. | |
| 5,713,917 A | 2/1998 | Leonhardt et al. | |
| 5,733,267 A | 3/1998 | Del Toro | |
| 5,733,325 A | 3/1998 | Robinson et al. | |
| 5,755,777 A | 5/1998 | Chuter | |
| 5,776,142 A | 7/1998 | Gunderson | |
| 5,782,855 A | 7/1998 | Lau et al. | |
| 5,788,707 A | 8/1998 | Del Toro et al. | |
| 5,797,952 A | 8/1998 | Klein | |
| 5,824,041 A | 10/1998 | Lenker et al. | |
| 5,824,058 A | 10/1998 | Ravenscroft et al. | |
| 5,860,955 A | 1/1999 | Wright et al. | |
| 5,902,334 A | 5/1999 | Dwyer et al. | |
| 5,906,619 A * | 5/1999 | Olson et al. | 606/108 |
| 5,935,161 A | 8/1999 | Robinson et al. | |
| 5,954,742 A | 9/1999 | Osypka | |
| 5,968,052 A | 10/1999 | Sullivan, III et al. | |
| 6,042,588 A | 3/2000 | Munsinger et al. | |
| 6,077,297 A | 6/2000 | Robinson et al. | |
| 6,110,151 A | 8/2000 | Spool et al. | |
| 6,117,142 A | 9/2000 | Goodson et al. | |
| 6,143,021 A | 11/2000 | Staehle | |
| 6,146,415 A | 11/2000 | Fitz | |
| 6,203,550 B1 | 3/2001 | Olson | |
| 6,251,132 B1 | 6/2001 | Ravenscroft et al. | |
| 6,395,017 B1 | 5/2002 | Dwyer et al. | |
| 6,468,298 B1 | 10/2002 | Pelton | |
| 6,488,700 B2 | 12/2002 | Klumb et al. | |
| 6,508,790 B1 | 1/2003 | Lawrence | |
| 6,514,261 B1 | 2/2003 | Randall et al. | |
| 6,520,986 B2 | 2/2003 | Martin et al. | |
| 6,656,212 B2 | 12/2003 | Ravenscroft et al. | |
| 6,660,030 B2 | 12/2003 | Shaolian et al. | |
| 6,676,692 B2 | 1/2004 | Rabkin et al. | |
| 6,764,503 B1 | 7/2004 | Ishimaru | |
| 6,843,802 B1 | 1/2005 | Villalobos et al. | |
| 6,911,039 B2 | 6/2005 | Shiu et al. | |
| 7,105,016 B2 | 9/2006 | Shiu et al. | |
| 7,264,632 B2 | 9/2007 | Wright et al. | |
| 7,419,501 B2 * | 9/2008 | Chiu et al. | 623/1.12 |
| 7,435,253 B1 | 10/2008 | Hartley et al. | |
| 7,803,177 B2 | 9/2010 | Hartley et al. | |
| 7,815,671 B2 | 10/2010 | Wright et al. | |
| 7,938,851 B2 * | 5/2011 | Olson et al. | 623/1.11 |
| 2002/0004676 A1 | 1/2002 | Berryman et al. | |
| 2002/0111666 A1 | 8/2002 | Hart et al. | |
| 2003/0074043 A1 | 4/2003 | Thompson | |
| 2003/0074045 A1 | 4/2003 | Buzzard et al. | |
| 2003/0199966 A1 | 10/2003 | Shiu et al. | |
| 2003/0233140 A1 | 12/2003 | Hartley et al. | |
| 2004/0093063 A1 | 5/2004 | Wright et al. | |
| 2004/0127912 A1 | 7/2004 | Rabkin et al. | |
| 2005/0080476 A1 | 4/2005 | Gunderson et al. | |
| 2005/0085888 A1 | 4/2005 | Andreas et al. | |
| 2005/0137612 A1 | 6/2005 | Assell et al. | |
| 2005/0228475 A1 | 10/2005 | Keeble et al. | |
| 2006/0085057 A1 | 4/2006 | George | |
| 2006/0276872 A1 | 12/2006 | Arbefeuille et al. | |
| 2007/0135818 A1 | 6/2007 | Moore et al. | |
| 2007/0156224 A1 * | 7/2007 | Cioanta et al. | 623/1.11 |
| 2007/0219616 A1 | 9/2007 | Modesitt et al. | |
| 2008/0077227 A1 | 3/2008 | Ouellette et al. | |
| 2008/0255651 A1 * | 10/2008 | Dwork | 623/1.11 |
| 2008/0262590 A1 | 10/2008 | Murray | |
| 2009/0254165 A1 * | 10/2009 | Tabor et al. | 623/1.11 |
| 2009/0319018 A1 * | 12/2009 | Moehl et al. | 623/1.11 |
| 2010/0030255 A1 | 2/2010 | Berra et al. | |
| 2011/0257718 A1 | 10/2011 | Argentine | |
| 2011/0270372 A1 * | 11/2011 | Argentine | 623/1.11 |

* cited by examiner

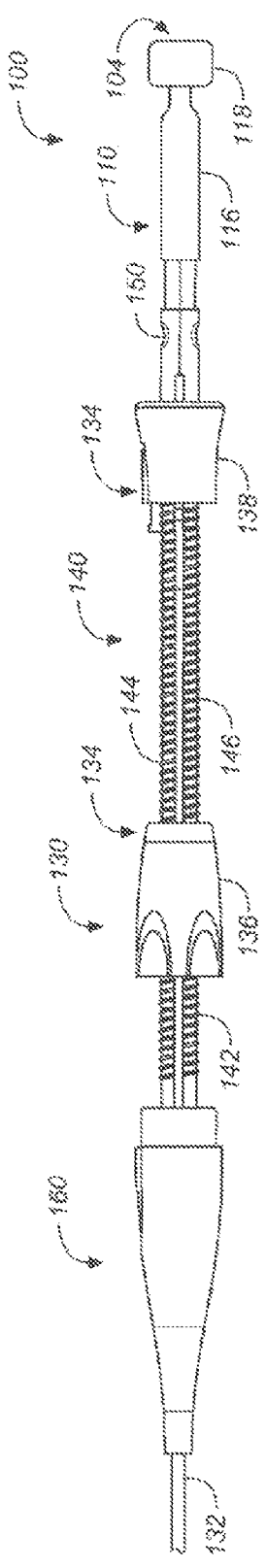
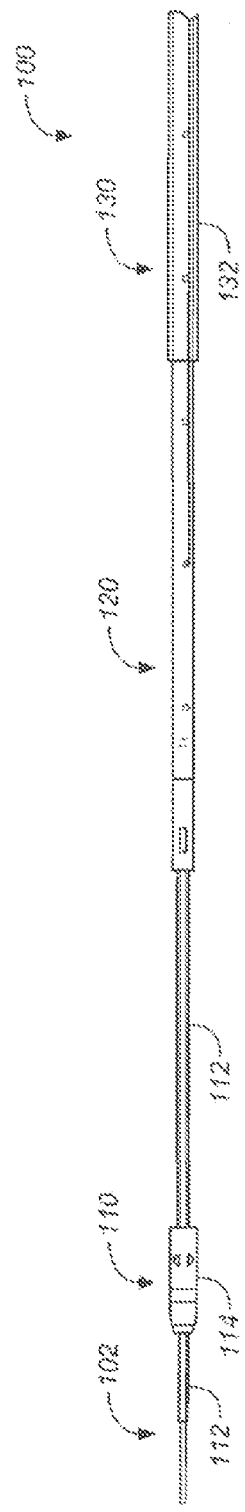
FIG. 1A
FIG. 1B

STENT GRAFT DELIVERY SYSTEM

TECHNICAL FIELD

The technical field of this disclosure is medical implantation devices, particularly, a stent graft delivery system.

BACKGROUND OF THE INVENTION

Stent grafts have been developed for the treatment of abdominal aortic aneurysms. An abdominal aortic aneurysm is a bulge that forms in the wall of the abdominal aorta, which is the main vessel of the arterial system of the body that extends through the abdomen. Abdominal aortic aneurysms can lose elasticity over time and rupture under normal blood pressure. A stent graft is a woven tube (graft) supported by a tubular metal stent. The stent graft is placed inside of an aneurysmal vessel to exclude the abdominal aortic aneurysm from normal blood flow and reduces pressure on the aneurysmal vessel.

Stent graft delivery systems are used to deliver the stent grafts to a deployment area inside the aorta. The stent graft can be inserted through a femoral artery and into the aorta. The stent graft can be enclosed within a sheath until the stent graft is in position at the deployment area, and then the sheath can be retracted to allow the stent graft to expand. The stent graft delivery system includes a number of complex parts because the clinician manipulates the stent graft remotely.

Presently, stent graft delivery systems include a large number of separate parts to meet the various performance requirements for stent graft deployment. For example, the sheath requires strain relief where it changes from being supported to being unsupported to prevent kinking at the transition point. The stent graft delivery system must also provide an interface near the transition point which allows the operator of the stent graft delivery system to grip and manipulate the sheath and the stent graft delivery system. The large number of separate parts must also be attached and/or connected to assemble the various parts into the stent graft delivery system. Unfortunately, the large number of separate parts required for the various functions increases manufacturing and inventory costs. Assembly time increases, increasing cost.

It would be desirable to have a stent graft delivery system that would overcome the above disadvantages.

SUMMARY OF THE INVENTION

One aspect according to the present invention provides a stent graft delivery system including a tip assembly having a tip tube; a middle member tube having a middle member proximal end and defining a middle member lumen, the tip tube being disposed in and axially slideable within the middle member lumen; a sheath assembly having a sheath tube and a sheath handle operably connected to a sheath tube proximal end, the sheath tube defining a sheath lumen, the middle member tube being disposed in and axially slideable within the sheath lumen; a threaded assembly having a threaded assembly distal end and defining an exterior thread, the threaded assembly having a first threaded tube portion and a second threaded tube portion; and a unitary front grip defining a proximal front grip lumen and a distal front grip lumen in communication with the proximal front grip lumen. The sheath tube is disposed in and axially slideable within the distal front grip lumen, the threaded assembly distal end is disposed in the proximal front grip lumen and fixed to the unitary front grip, the first threaded tube portion and the second threaded tube portion being radially compressed together by the unitary front grip. The sheath handle engages the exterior thread of the threaded assembly in a first configuration to move the sheath tube axially relative to the middle member tube and tip tube through rotation of the sheath handle and disengages the exterior thread of the threaded assembly in a second configuration to move the sheath tube axially relative to the middle member tube and tip tube through axial motion of the sheath handle.

Another aspect according to the present invention provides a unitary front grip for use in a stent graft delivery system having a sheath tube, and a threaded assembly having a first threaded tube portion and a second threaded tube portion. The unitary front grip includes a front grip strain relief portion defining a distal front grip lumen; and a front grip body portion axially adjacent the front grip strain relief portion, the front grip body portion defining a proximal front grip lumen. The distal front grip lumen is sized to slideably receive the sheath tube, the proximal front grip lumen is sized to receive the threaded assembly, and the front grip body portion is sized to compress together the first threaded tube portion and the second threaded tube portion.

Another aspect according to the present invention provides a stent graft delivery system including a tip assembly having a tip tube and a tip handle operably connected to a tip tube proximal end, the tip tube defining a guidewire lumen; a middle member tube having a middle member proximal end and defining a middle member lumen, the tip tube being disposed in and axially slideable within the middle member lumen; a sheath assembly having a sheath tube and a sheath handle operably connected to a sheath tube proximal end, the sheath tube defining a sheath lumen, the middle member tube being disposed in and axially slideable within the sheath lumen; a threaded assembly having a threaded assembly distal end and defining an exterior thread, the threaded assembly having a first threaded tube portion and a second threaded tube portion; and a unitary front grip defining a front grip lumen having a proximal portion and a distal portion, the unitary front grip having a champagne bottle-shaped exterior and being made of a resilient silicone material. The sheath tube is disposed in and axially slideable within the distal portion of the front grip lumen, the threaded assembly distal end is disposed in the proximal portion of the front grip lumen and fixed to the unitary front grip, the first threaded tube portion and the second threaded tube portion being radially compressed together by the unitary front grip. The sheath handle engages the exterior thread of the threaded assembly in a first configuration to move the sheath tube axially relative to the middle member tube and tip tube through rotation of the sheath handle and disengages the exterior thread of the threaded assembly in a second configuration to move the sheath tube axially relative to the middle member tube and tip tube through axial motion of the sheath handle.

The foregoing and other features and advantages will become further apparent from the following detailed description of the presently preferred embodiments, read in conjunction with the accompanying drawings

BRIEF DESCRIPTION OF THE DRAWINGS

FIGS. 1A & 1B are side views of a stent graft delivery system made in accordance with the present invention;

DETAILED DESCRIPTION

Figure 2A:
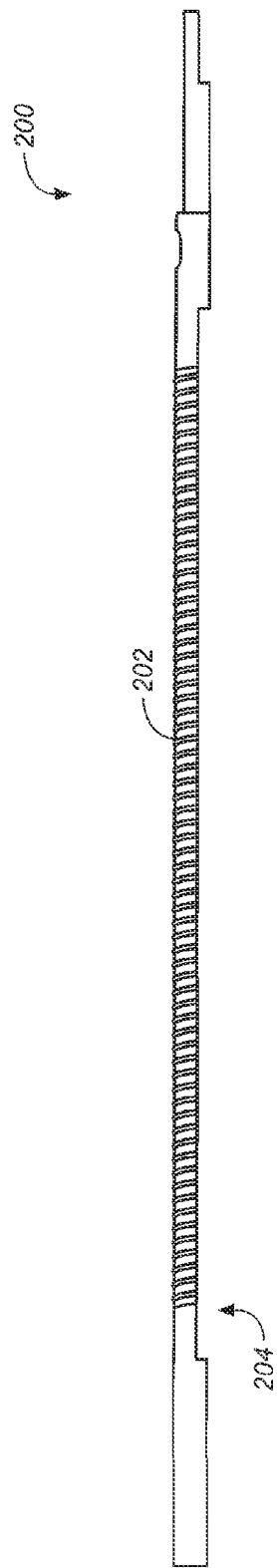
FIGS. 2A & 2B are side and top views, respectively, of a threaded tube portion of a stent graft delivery system made in accordance with the present invention.

FIGS. 1A & 1B, in which like elements share like reference numbers, are side views of a stent graft delivery system made in accordance with the present invention. The stent graft delivery system 100 includes a tip assembly 110, a middle member tube 120, a sheath assembly 130, a threaded assembly 140, a unitary encloseal 150, and a unitary front grip 160. The distal end 102 of the stent graft delivery system 100 is inserted in a vessel to deliver the stent graft and the proximal end 104 of the stent graft delivery system 100 remains outside the patient. As used herein, distal and proximal are defined from the viewpoint of the operator of the stent graft delivery system 100 with the proximal end 104 nearer the operator.

The tip assembly 110 includes a tip tube 112, a stent graft retainer 114 operably connected to the distal end of the tip tube 112, and a tip handle 118 operably connected to the proximal end of the tip tube 112. The tip tube 112 can define a guidewire lumen axially along the interior of the tip tube 112. The stent graft delivery system 100 can follow a guidewire deployed in the vasculature of the patient to the stent graft deployment site by inserting the guidewire in the guidewire lumen. The middle member tube 120 has a middle member proximal end and defines a middle member lumen axially along the interior of the middle member tube 120. The tip tube 112 is disposed in and axially slideable within the middle member lumen.

The sheath assembly 130 includes a sheath tube 132 and a sheath handle 134 operably connected to a sheath tube proximal end. The sheath tube 132 defines a sheath lumen axially along the interior of the sheath tube 132. The middle member tube 120 is disposed in and axially slideable within the sheath lumen. In this example, the sheath handle 134 includes a rotatable sheath handle 136 and a slideable sheath handle 138, which include complementary fittings so that the rotatable sheath handle 136 and the slideable sheath handle 138 can be connected into a single sheath handle while still allowing rotation of the rotatable sheath handle 136.

The threaded assembly 140 has an exterior thread 142 and defines a threaded assembly lumen, a first sidewall port, and a second sidewall port. The threaded assembly 140 can include first threaded tube portion 144 and a second threaded tube portion 146. The unitary front grip 160 and/or unitary rear grip 116 can compress the first threaded tube portion 144 and a second threaded tube portion 146 together to form the threaded assembly 140. The unitary front grip 160 and/or unitary rear grip 116 can be made of a resilient material, such as a resilient silicone material or a resilient silicone material having a Shore A durometer hardness of 40 to 50. The sheath handle 134 engages the exterior thread 142 of the threaded assembly 140 in a first configuration to move the sheath tube 132 axially relative to the middle member tube 120 and tip tube 112 through rotation of the sheath handle 134. The sheath handle 134 disengages the exterior thread 142 of the threaded assembly 140 in a second configuration to move the sheath tube 132 axially relative to the middle member tube 120 and tip tube 112 through axial motion of the sheath handle 134.

The unitary encloseal 150 includes an axial cylindrical encloseal body and a transverse cylindrical encloseal body. Portions of the transverse cylindrical encloseal body are disposed in the first and second sidewall ports of the threaded assembly 140. The axial cylindrical encloseal body is disposed in the threaded assembly lumen. The tip tube 112 is disposed in and axially slideable within a portion of an encloseal lumen. The middle member proximal end of the middle member tube 120 is disposed in another portion of the encloseal lumen and fixed to the axial cylindrical encloseal body. As used herein, unitary is defined as being a single, whole part, and not a part assembled from other parts.

The unitary front grip 160 defines a front grip lumen. The first threaded tube portion 144 and the second threaded tube portion 146 are radially compressed together by the unitary front grip 160 in the front grip lumen. The sheath tube 132 is disposed in and axially slideable within a portion of a front grip lumen. The distal end of the threaded assembly 140 is disposed in another portion of the front grip lumen and fixed to the unitary front grip 160. In this example, the unitary front grip 160 has a champagne bottle-shaped exterior. As used herein, unitary is defined as being a single, whole part, and not a part assembled from other parts.

In operation, a stent graft is loaded onto the stent graft delivery system 100 over the tip tube 112 between the stent graft retainer 114 and the middle member tube 120. The sheath tube 132 is advanced distally over the stent graft to the stent graft retainer 114 to locate the stent graft within the lumen of the sheath tube 132 and hold the stent graft in a compressed configuration. The rotatable sheath handle 136 and the slideable sheath handle 138 of the sheath handle 134 are coupled together.

A guidewire is positioned in the vasculature of the patient and the stent graft delivery system 100 advanced through the vasculature over the guidewire until the stent graft is at the deployment site, such as in an aortic aneurysm. The operator grasps the unitary front grip 160 and rotates the rotatable sheath handle 136 to gradually withdraw the sheath tube 132 and release the distal portion of the stent graft. When the distal portion of the stent graft is satisfactorily seated, the rotatable sheath handle 136 and the slideable sheath handle 138 can be uncoupled from each other. The operator slides the slideable sheath handle 138 axially to aggressively withdraw the sheath tube 132 and release the remaining portion of the stent graft. When the whole stent graft has been deployed, the operator is now ready to release the Tip Capture which has been holding the struts of the stent in abeyance. This is accomplished by pushing the unitary rear grip 116 forward which moves the stent graft retainer 114 off the stent struts allowing them to embed into the wall of the vessel fixing the device. With the stent graft deployed the Tip Capture Mechanism is prepared for retraction by pulling the unitary rear grip 116 back into its original position. This done, the entire Delivery System may be removed from the vasculature.

Figure 2B:
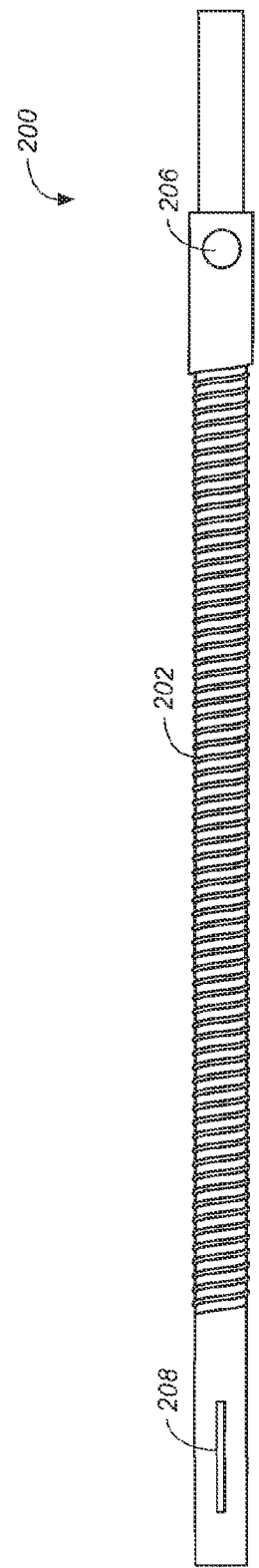

FIGS. 2A & 2B, in which like elements share like reference numbers, are side and top views, respectively, of a threaded tube portion of a stent graft delivery system made in accordance with the present invention. A pair of threaded tube portions can be combined to form a threaded assembly. The threaded tube portion 200 includes an exterior thread 202 that can be engaged by the sheath handle to gradually move the sheath axially through rotation of the sheath handle. The sheath moves within the threaded assembly lumen defined within the pair of threaded tube portions. In one embodiment, the threaded tube portion 200 includes an edge slot 204 to allow a portion of the sheath handle to pass from outside the threaded assembly and connect to the sheath within the threaded assembly lumen. The threaded tube portion 200 can also define a sidewall port 206 and/or a front grip alignment slot 208. The sidewall ports receive a portion of the unitary encloseal, which helps to align the threaded tube portions into the threaded assembly and can provide access for flushing the middle member lumen. The front grip alignment slots receive a portion of the unitary front grip to align and prevent rotation of the unitary front grip.

Figure 3A:
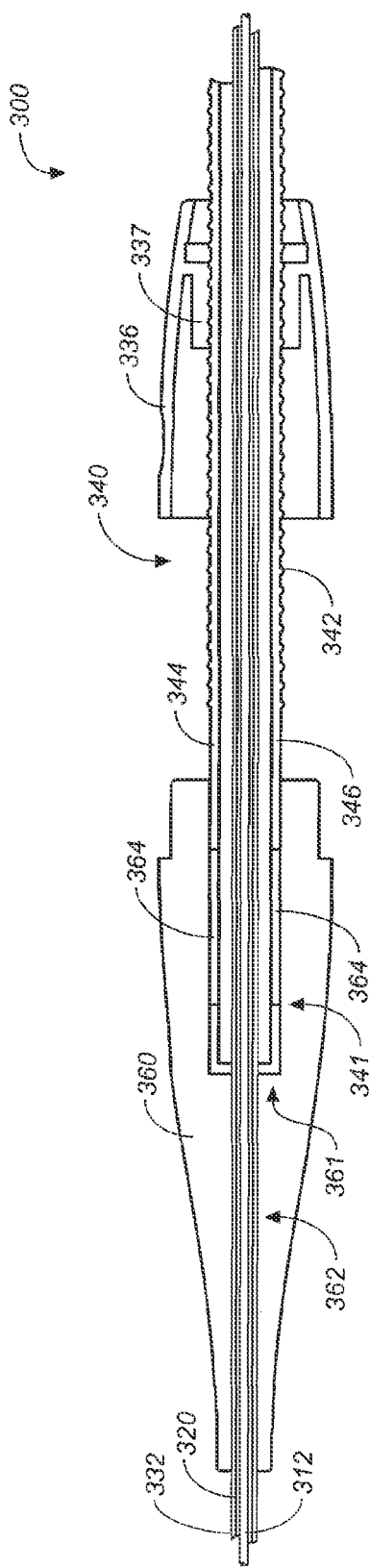
FIGS. 3A & 3B are detailed cross section side views of a stent graft delivery system made in accordance with the present invention.
Figure 3B:
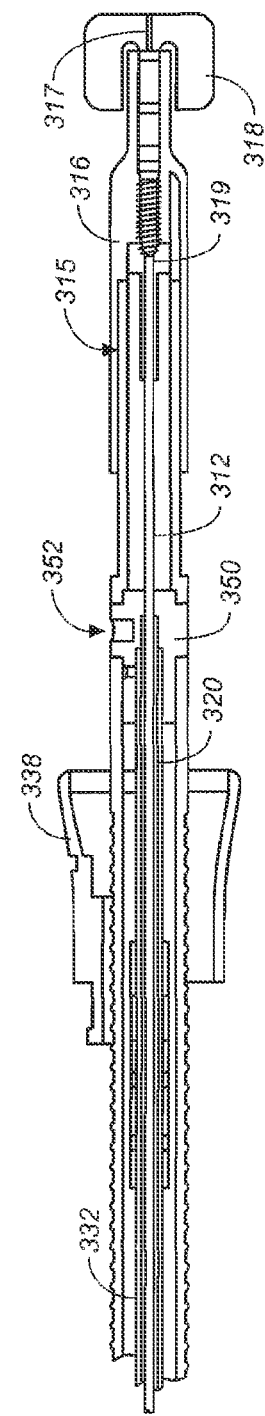

FIGS. 3A & 3B, in which like elements share like reference numbers, are detailed cross section side views of a stent graft delivery system made in accordance with the present invention. In the stent graft delivery system 300, the tip tube 312 is disposed in the middle member tube 320, which is disposed in the sheath tube 332. The proximal end of the tip tube 312 terminates at a connection 319 to the tip handle 318 with the guidewire lumen 317 continuing through the tip handle 318. The tip tube 312 enters the middle member tube 320 at the unitary endoseal 350. The proximal end of the middle member tube 320 terminates at the unitary endoseal 350, where the middle member tube 320 receives the tip tube 312. A flush port 352 defined by the middle member tube 320 is in fluid communication with the middle member lumen when a flush connector is inserted into the flush port 352 to allow flushing of the middle member lumen. The proximal end of the sheath tube 332 terminates at the slideable sheath handle 338. The sheath tube 332 is slideable within the distal front grip lumen 362 defined by the unitary front grip 360. Alignment tabs 364 in the unitary front grip 360 extend into front grip alignment slots 341 in the first threaded tube portion 344 and second threaded tube portion 346.

The unitary front grip 360 and the unitary rear grip 316 hold together the threaded assembly 340. The proximal front grip lumen 361 defined by the unitary front grip 360 receives the distal ends of the first threaded tube portion 344 and second threaded tube portion 346. The unitary front grip 360 compresses the first threaded tube portion 344 and second threaded tube portion 346 together. The distal rear grip lumen 315 defined by the unitary rear grip 316 receives the proximal ends of the first threaded tube portion 344 and second threaded tube portion 346. The unitary rear grip 316 compresses the first threaded tube portion 344 and second threaded tube portion 346 together.

An inside threaded portion 337 of the rotatable sheath handle 336 engages the exterior thread 342 of the threaded assembly 340. When the rotatable sheath handle 336 and the slideable sheath handle 338 are coupled, the rotation of the rotatable sheath handle 336 moves the slideable sheath handle 338 axially, moving the sheath tube 332. When the rotatable sheath handle 336 and the slideable sheath handle 338 are uncoupled, the axial motion of the slideable sheath handle 338 moving the sheath tube 332 axially, independent of the rotatable sheath handle 336. Thus, the sheath handle engages the exterior threads in a first configuration with the rotatable sheath handle 336 and the slideable sheath handle 338 coupled and disengages the exterior threads in a second configuration with the rotatable sheath handle 336 and the slideable sheath handle 338 uncoupled. Those skilled in the art will appreciate that the action of the rotatable sheath handle and slideable sheath handle are exemplary and that the axial displacement of the sheath tube can be accomplished with other sheath handle mechanisms as desired for a particular application.

Figure 4A:
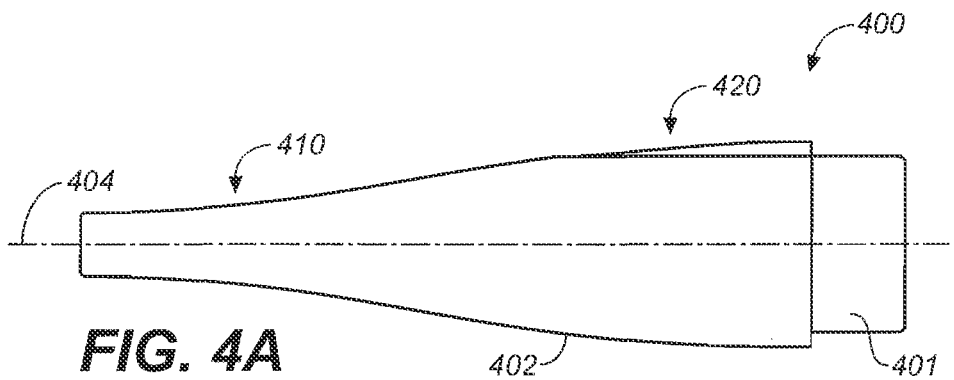
FIGS. 4A-4D are various views of a unitary front grip of a stent graft delivery system made in accordance with the present invention.
Figure 4B:
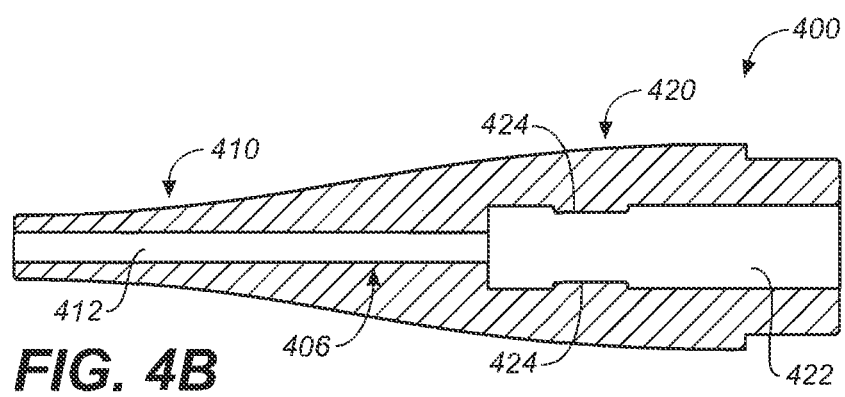
Figure 4C:
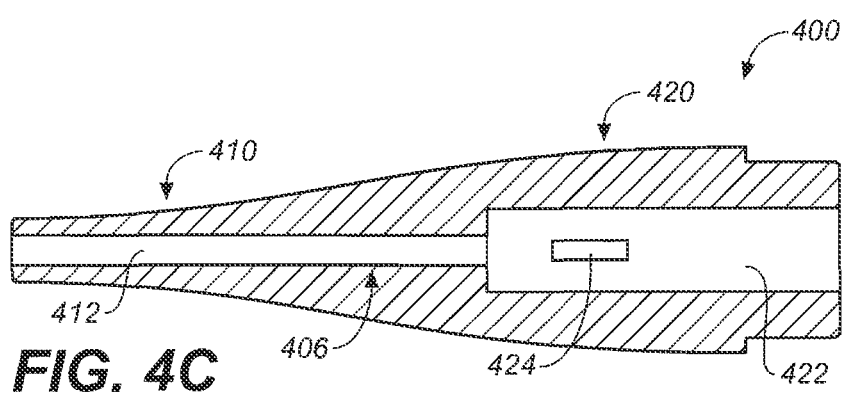

FIGS. 4A-4C, in which like elements share like reference numbers, are various views of a unitary front grip of a stent graft delivery system made in accordance with the present invention. FIG. 4A is a side view, FIG. 4B is an axial cross section side view, FIG. 4C is an axial cross section top view, and FIG. 4D is an axial cross section side view including the sheath tube and threaded assembly.

Referring to FIG. 4A, the unitary front grip 400 is for use in a stent graft delivery system having a sheath tube, and a threaded assembly having a first threaded tube portion and a second threaded tube portion. The unitary front grip 400 has a front grip strain relief portion 410 and a front grip body portion 420 axially adjacent the front grip strain relief portion 410. The front grip strain relief portion 410 flexes way from the central axis 404 when force is applied by the sheath tube passing through the front grip strain relief portion 410, easing the stress on the sheath tube and avoiding kinking. In one embodiment, the unitary front grip 400 includes an optional proximal cylindrical portion 401 mateable with a distal portion of a sheath handle The unitary front grip 400 has a champagne bottle-shaped exterior. Champagne bottle-shaped as used herein is defined as a generally elongated truncated conical shape in which an axially bisecting plane intersecting the exterior surface of the unitary front grip 400 is a compound curve 402 tending to parallel the central axis 404 of the unitary front grip 400 toward the ends of the unitary front grip 400. In one embodiment, the unitary front grip 400 has a textured exterior to give the operator better grip and control. The pattern of the textured exterior can be selected as desired for a particular application. The unitary front grip 400 can be formed of any resilient material as desired for a particular application. In one embodiment, the unitary front grip 400 is a resilient silicone material. In one embodiment, the resilient silicone material has a Shore A durometer hardness of 40 to 50.

Figure 4D:
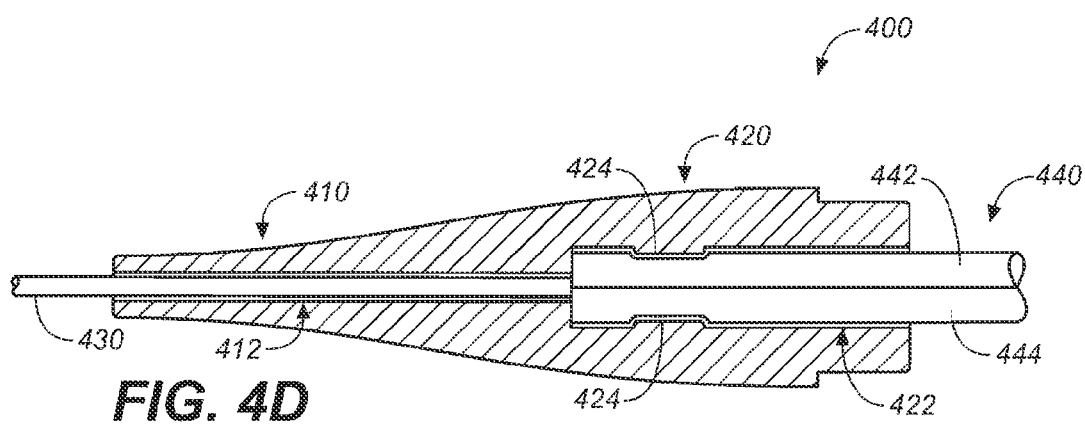

Referring to FIGS. 4B-4D, the unitary front grip 400 defines a front grip lumen 406 axially through the unitary front grip 400. The front grip strain relief portion 410 defines a distal front grip lumen 412 and the front grip body portion 420 defines a proximal front grip lumen 422. The distal front grip lumen 412 is sized to slideably receive the sheath tube 430, the proximal front grip lumen 422 is sized to receive the threaded assembly 440, and the front grip body portion 420 is sized to compress together the first threaded tube portion 442 and the second threaded tube portion 444 of the threaded assembly 440.

The unitary front grip 400 can include one or more alignment tabs 424 projecting into the proximal front grip lumen 422 to assist in aligning and retaining the unitary front grip 400 with the threaded tube portions of the threaded assembly 440. The threaded tube portions 442, 444 include front grip alignment slots sized complementary to the alignment tabs 424. In one embodiment, adhesive is used in addition to the alignment tabs 424 to fix the threaded assembly distal end to the unitary front grip 400. In another embodiment, the alignment tabs are omitted and friction between the threaded assembly distal end and the unitary front grip 400 fixes the threaded assembly distal end to the unitary front grip 400. In yet another embodiment, the alignment tabs are omitted and adhesive is used to fix the threaded assembly distal end to the unitary front grip 400.

While specific embodiments of the invention are disclosed herein, various changes and modifications can be made without departing from the spirit and scope of the invention. The scope of the invention is indicated in the appended claims, and all changes that come within the meaning and range of equivalents are intended to be embraced therein.

The invention claimed is:

1. A stent graft delivery system comprising:
a tip assembly having a tip tube;
a middle member tube having a middle member proximal end and defining a middle member lumen, the tip tube being disposed in and axially slideable within the middle member lumen;
a sheath assembly having a sheath tube and a sheath handle operably connected to a sheath tube proximal end, the sheath tube defining a sheath lumen, the middle member tube being disposed in and axially slideable within the sheath lumen;

a threaded assembly having a threaded assembly distal end and defining an exterior thread, the threaded assembly having a first threaded tube portion, a second threaded tube portion, and a longitudinal slot disposed between the first threaded tube portion and the second threaded tube portion; and a unitary front grip defining a proximal front grip lumen and a distal front grip lumen in communication with the proximal front grip lumen, wherein at least a portion of the longitudinal slot is disposed proximal of the unitary front grip;

wherein the sheath tube is disposed in and axially slideable within the distal front grip lumen, the threaded assembly distal end is disposed in the proximal front grip lumen and fixed to the unitary front grip, and the first threaded tube portion and the second threaded tube portion are radially compressed together by the unitary front grip; and wherein the sheath handle engages the exterior thread of the threaded assembly in a first configuration to move the sheath tube axially relative to the middle member tube and tip tube through rotation of the sheath handle and disengages the exterior thread of the threaded assembly in a second configuration to move the sheath tube axially relative to the middle member tube and tip tube through axial motion of the sheath handle.

2. The stent graft delivery system of claim 1 wherein the unitary front grip has a champagne bottle-shaped exterior.

3. The stent graft delivery system of claim 1 wherein the unitary front grip has a textured exterior.

4. The stent graft delivery system of claim 1 wherein the unitary front grip includes a first alignment tab and a second alignment tab projecting into the proximal portion of the front grip lumen, the first threaded tube portion defines a first front grip alignment slot, the second threaded tube portion defines a second front grip alignment slot, the first alignment tab is disposed in the first front grip alignment slot, and the second alignment tab is disposed in the second front grip alignment slot.

5. The stent graft delivery system of claim 1 wherein the unitary front grip comprises a resilient silicone material.

6. The stent graft delivery system of claim 5 wherein the resilient silicone material has a Shore A durometer hardness of 40 to 50.

7. The stent graft delivery system of claim 1 wherein the unitary front grip includes a proximal cylindrical portion mateable with a distal portion of the sheath handle.

8. The stent graft delivery system of claim 1 wherein the threaded assembly distal end is fixed to the unitary front grip by friction between the threaded assembly distal end and the unitary front grip.

9. The stent graft delivery system of claim 1 wherein the threaded assembly distal end is fixed to the unitary front grip with an adhesive.

10. The stent graft delivery system of claim 1 further comprising a unitary rear grip disposed about a proximal end of the threaded assembly, the first threaded tube portion and the second threaded tube portion being radially compressed together by the unitary rear grip.

11. The stent graft delivery system of claim 10 wherein the unitary rear grip comprises a resilient silicone material having a Shore A durometer hardness of 40 to 50.

12. The stent graft delivery system of claim 1 wherein the tip tube defines a guidewire lumen.

13. A stent graft delivery system comprising:

a tip assembly having a tip tube and a tip handle operably connected to a tip tube proximal end, the tip tube defining a guidewire lumen;

a middle member tube having a middle member proximal end and defining a middle member lumen, the tip tube being disposed in and axially slideable within the middle member lumen;

a sheath assembly having a sheath tube and a sheath handle operably connected to a sheath tube proximal end, the sheath tube defining a sheath lumen, the middle member tube being disposed in and axially slideable within the sheath lumen;

a threaded assembly having a threaded assembly distal end and defining an exterior thread, the threaded assembly having a first threaded tube portion, a second threaded tube portion, and a longitudinal slot disposed between the first threaded tube portion and the second threaded tube portion; and a unitary front grip defining a front grip lumen having a proximal portion and a distal portion, the unitary front grip having a champagne bottle-shaped exterior and comprising a resilient silicone material, wherein at least a portion of the longitudinal slot is disposed proximal of the unitary front grip;

wherein the sheath tube is disposed in and axially slideable within the distal portion of the front grip lumen, the threaded assembly distal end is disposed in the proximal portion of the front grip lumen and fixed to the unitary front grip, and the first threaded tube portion and the second threaded tube portion are radially compressed together by the unitary front grip; and wherein the sheath handle engages the exterior thread of the threaded assembly in a first configuration to move the sheath tube axially relative to the middle member tube and tip tube through rotation of the sheath handle and disengages the exterior thread of the threaded assembly in a second configuration to move the sheath tube axially relative to the middle member tube and tip tube through axial motion of the sheath handle.

* * * * *